US009381080B2

(12) United States Patent
Benz et al.

(10) Patent No.: US 9,381,080 B2
(45) Date of Patent: Jul. 5, 2016

(54) HYDROPHOBIC INTRAOCULAR LENS

(75) Inventors: Patrick H. Benz, Sarasota, FL (US); Adam Reboul, Sarasota, FL (US)

(73) Assignee: Benz Research and Development Corp., Sarasota, FL (US)

( * ) Notice: Subject to any disclaimer, the term of this patent is extended or adjusted under 35 U.S.C. 154(b) by 82 days.

(21) Appl. No.: 13/618,894

(22) Filed: Sep. 14, 2012

(65) Prior Publication Data

US 2013/0253159 A1    Sep. 26, 2013

Related U.S. Application Data

(60) Provisional application No. 61/535,795, filed on Sep. 16, 2011.

(51) Int. Cl.

| *C08F 20/18* | (2006.01) |
| *C08F 20/20* | (2006.01) |
| *C08F 20/36* | (2006.01) |
| *A61F 2/16* | (2006.01) |
| *A61L 27/16* | (2006.01) |
| *C08F 220/30* | (2006.01) |
| *C08F 220/28* | (2006.01) |

(52) U.S. Cl.
CPC . *A61F 2/16* (2013.01); *A61L 27/16* (2013.01); *C08F 220/30* (2013.01); *A61L 2430/16* (2013.01); *C08F 220/28* (2013.01); *C08F 2220/285* (2013.01)

(58) Field of Classification Search
CPC .......... C08F 20/12; C08F 20/18; C08F 20/28; C08F 20/20; C08F 220/10; C08F 220/12; C08F 220/18; C08F 220/20; C08F 220/28; C08F 220/30; A61L 27/16; A61F 9/0017; A61F 2/16
See application file for complete search history.

(56) References Cited

U.S. PATENT DOCUMENTS

| 5,326,506 | A | 7/1994 | Vanderbilt | |
| 5,693,095 | A * | 12/1997 | Freeman et al. | 623/6.56 |
| 6,267,784 | B1 | 7/2001 | Benz et al. | |
| 6,353,069 | B1 * | 3/2002 | Freeman et al. | 526/319 |
| 6,365,685 | B1 | 4/2002 | Collina et al. | |
| 6,517,750 | B2 | 2/2003 | Benz et al. | |
| 7,067,602 | B2 | 6/2006 | Benz et al. | |
| 7,387,642 | B2 | 6/2008 | Benz et al. | |
| 7,947,796 | B2 | 5/2011 | Benz et al. | |
| 2002/0027302 | A1 | 3/2002 | Benz et al. | |
| 2002/0058723 | A1 | 5/2002 | Benz et al. | |
| 2002/0058724 | A1 | 5/2002 | Benz et al. | |
| 2005/0131183 | A1 | 6/2005 | Benz et al. | |
| 2006/0110427 | A1 * | 5/2006 | Molock et al. | 424/427 |
| 2006/0199929 | A1 | 9/2006 | Benz et al. | |
| 2006/0276606 | A1 | 12/2006 | Benz et al. | |
| 2008/0081851 | A1 * | 4/2008 | Benz et al. | 523/113 |
| 2008/0221235 | A1 | 9/2008 | Benz et al. | |

FOREIGN PATENT DOCUMENTS

| CN | 1155845 A | 7/1997 |
| CN | 1353726 A | 6/2002 |
| CN | 1371394 A | 9/2002 |
| WO | WO-96/40303 | 12/1996 |
| WO | WO 00/79312 A1 * | 12/2000 |
| WO | WO-00/79312 A1 | 12/2000 |
| WO | WO-01/18079 | 3/2001 |
| WO | WO-01/18079 A1 | 3/2001 |
| WO | WO-2006/113290 A1 | 10/2006 |
| WO | WO-2010/128266 A1 | 11/2010 |

OTHER PUBLICATIONS

Garcia et al., "Reaction Kinetics and Gel Effect on the Polymerization of 2-Ethoxyethyl Methacrylate and 2(2-Ethoxyethoxy) Ethyl Methacrylate," Journal of Polymer Science Part A: Polymer Chemistry, 2002, vol. 40, pp. 3987-4001.
International Preliminary Report on Patentability in International Application No. PCT/US2012/05540 issued Mar. 18, 2014.
International Search Report and Written Opinion for PCT/US2012/055540, mailing date Nov. 22, 2012, 8 pages.
Notification of First Office Action mailed Apr. 21, 2015 in China Appln. No. 2015041601037540, with translation.

* cited by examiner

*Primary Examiner* — Karuna P Reddy
(74) *Attorney, Agent, or Firm* — Foley & Lardner LLP

(57) ABSTRACT

An intraocular lens (IOL) with excellent non-glistening characteristics comprising at least one copolymer comprising: (a) one or more first monomeric subunits comprising a polymerized acrylate and/or methacrylate group, at least one side group comprising (i) an aryloxy moiety, and (ii) an aliphatic carbon moiety linking the aryloxy moiety with the polymerized acrylate or methacrylate group, wherein the aliphatic carbon moiety comprises at least one hydroxyl substituent, (b) one or more second monomeric subunits different from the first monomeric subunits comprising a polymerized acrylate and/or methacrylate group, and comprising at least one alkoxyalkyl side group, (c) one or more third monomeric subunits different from the first and second monomeric subunits, the third monomeric subunits comprising a polymerized acrylate and/or methacrylate group, and comprising at least one alkylene oxide side group, wherein the first monomeric subunit is present in a greater amount by weight than the second monomeric subunit, and the first and second monomeric subunits together comprise about 75 percent or more of the monomeric subunits composition by weight.

27 Claims, 7 Drawing Sheets

HYDROPHOBIC INTRAOCULAR LENS

RELATED APPLICATIONS

This application claims priority to U.S. provisional application Ser. No. 61/535,795 filed Sep. 16, 2011, the complete disclosure of which is hereby incorporated by reference in its entirety.

BACKGROUND

Various types of intraocular lenses (IOLs) are known. For example, there are known one-piece intraocular lenses and composite intraocular lens having multiple pieces. A one-piece intraocular lens is one where both optic and non-optic portions are made from one material. The non-optic portions of IOLs are referred to as haptic portions, and are used for attachment purposes.

Both hydrophobic and hydrophilic foldable IOLs are described in the prior art in, for example, U.S. Pat. Nos. 7,947,796, 7,387,642, 7,067,602, 6,517,750 and 6,267,784 each of which is hereby incorporated by reference in its entirety. See also, for example, U.S. Patent Publication Nos. 2008/0221235, 2006/0276606, 2006/0199929, 2005/0131183, 2002/0058724, 2002/0058723 and 2002/0027302 each of which is hereby incorporated by reference in its entirety.

Additionally, lens materials comprising the monomer 2-hydroxy-3-phenoxypropyl acrylate are disclosed in the prior art in, for example, WO 2010/128266, WO 2001/018079, WO 2000/079312, WO 96/40303, and U.S. Pat. No. 5,693,095. The lens material 2-ethoxyethyl methacrylate is also known in the art as a compound with a low glass transition temperature. See, for example, Garcia, F., et al., *J. of Polymer Science: Part A: Polymer Chemistry*, Vol. 40, 3987-4001 (2002).

A need exists, however, for better IOL materials including hydrophobic materials, which do not suffer from excessive glistening, can provide an absence of stickiness characteristics after injection of the IOL, and can provide for difficult-to-achieve combinations of properties.

SUMMARY

Embodiments described herein include, for example, copolymers, lenses, intraocular lenses, blanks for intraocular lenses, and methods for making and methods of using compositions and intraocular lenses.

One embodiment provides, for example, an intraocular lens comprising at least one copolymer comprising: (a) one or more first monomeric subunits comprising a polymerized acrylate or methacrylate group, at least one side group comprising (i) an aryloxy moiety, and (ii) an aliphatic carbon moiety linking the aryloxy moiety with the polymerized acrylate or methacrylate group, wherein the aliphatic carbon moiety comprises at least one hydroxyl substituent, and (b) one or more second monomeric subunits different from the first monomeric subunits comprising a polymerized acrylate or methacrylate group, and comprising at least one alkoxyalkyl side group, (c) one or more third monomeric subunits different from the first and second monomeric subunits, the third monomeric subunits comprising a polymerized acrylate or methacrylate group, and comprising at least one alkylene oxide side group, wherein the first monomeric subunit is present in a greater amount by weight than the second monomeric subunit, and the first and second monomeric subunits together comprise about 75 percent or more of the monomeric subunits composition by weight.

A composition comprising at least one copolymer comprising: (a) one or more first monomeric subunits comprising a polymerized acrylate or methacrylate group, at least one side group comprising (i) an aryloxy moiety, and (ii) an aliphatic carbon moiety linking the aryloxy moiety with the polymerized acrylate or methacrylate group, wherein the aliphatic carbon moiety comprises at least one hydroxyl substituent, and (b) one or more second monomeric subunits different from the first monomeric subunits comprising a polymerized acrylate or methacrylate group, and comprising at least one alkoxyalkyl side group, (c) one or more third monomeric subunits different from the first and second monomeric subunits, the third monomeric subunits comprising a polymerized acrylate or methacrylate group, and comprising at least one alkylene oxide side group, wherein the first monomeric subunit is present in a greater amount by weight than the second monomeric subunit, and the first and second monomeric subunits together comprise about 75 percent or more of the monomeric subunits composition by weight.

A method for making a composition comprising at least one copolymer comprising monomeric subunits comprising: preparing a co-monomer mixture comprising: (a) one or more first monomers comprising a polymerizable acrylate or methacrylate group, at least one side group comprising (i) an aryloxy moiety, and (ii) an aliphatic carbon moiety linking the aryloxy moiety with the polymerizable acrylate or methacrylate group, wherein the aliphatic carbon moiety comprises at least one hydroxyl substituent, and (b) one or more second monomers different from the first monomer(s) comprising a polymerizable acrylate or methacrylate group, and comprising at least one alkoxyalkyl side group, (c) one or more third monomers different from the first and second monomers, the third monomers comprising a polymerizable acrylate or methacrylate group, and comprising at least one alkylene oxide side group, wherein the first monomer(s) is present in a greater amount by weight than the second monomer(s), and the first and second monomers together comprise about 75 percent or more of the monomers by weight; polymerizing the co-monomer mixture.

An intraocular lens comprising at least one copolymer consisting essentially of: (a) one or more first monomeric subunits consisting essentially of a polymerized acrylate or methacrylate group, at least one side group comprising (i) an aryloxy moiety, and (ii) an aliphatic carbon moiety linking the aryloxy moiety with the polymerized acrylate or methacrylate group, wherein the aliphatic carbon moiety consists essentially of at least one hydroxyl substituent, and (b) one or more second monomeric subunits different from the first monomeric subunits consisting essentially of a polymerized acrylate or methacrylate group, and consisting essentially of at least one alkoxyalkyl side group, (c) one or more third monomeric subunits different from the first and second monomeric subunits, the third monomeric subunits consisting essentially of a polymerized acrylate and/or methacrylate group, and consisting essentially of at least one alkylene oxide side group, (d) one or more fourth monomeric subunits different from the first, second, and third monomeric subunits which are crosslinked subunits, wherein the first monomeric subunit is present in a greater amount by weight than the second monomeric subunit, and the first and second monomeric subunits together consist essentially of about 75 percent or more of the monomeric subunits composition by weight.

A composition comprising a co-monomer mixture comprising: (a) one or more first monomers comprising a polymerizable acrylate or methacrylate group, at least one side group comprising (i) an aryloxy moiety, and (ii) an aliphatic carbon moiety linking the aryloxy moiety with the polymerizable acrylate or methacrylate group, wherein the aliphatic carbon moiety comprises at least one hydroxyl substituent, and (b) one or more second monomers different from the first monomer(s) comprising a polymerizable acrylate or methacrylate group, and comprising at least one alkoxyalkyl side group, (c) one or more third monomers different from the first and second monomers, the third monomers comprising a polymerizable acrylate or methacrylate group, and comprising at least one alkylene oxide side group, wherein the first monomer(s) is present in a greater amount by weight than the second monomer(s), and the first and second monomers together comprise about 75 percent or more of the monomers by weight.

At least one advantage for at least one embodiment includes excellent non-glistening properties for an IOL, particularly for a hydrophobic IOL.

At least one additional advantage for at least one embodiment includes good unfolding properties for an IOL. For example, an IOL embodied herein may unfold in five to ten seconds.

At least one additional advantage for at least one embodiment includes an absence of stickiness characteristics after injection of the IOL (e.g., the haptic does not stick to the optic).

At least one additional advantage for at least one embodiment includes a refractive index of greater than 1.50 in combination with very low glistening.

Yet another advantage for at least one embodiment is a high diopter IOL able to pass through a small orifice injector, such as a 1.8 mm or lower Medicel injector.

DETAILED DESCRIPTION

Introduction

Figure 1A:
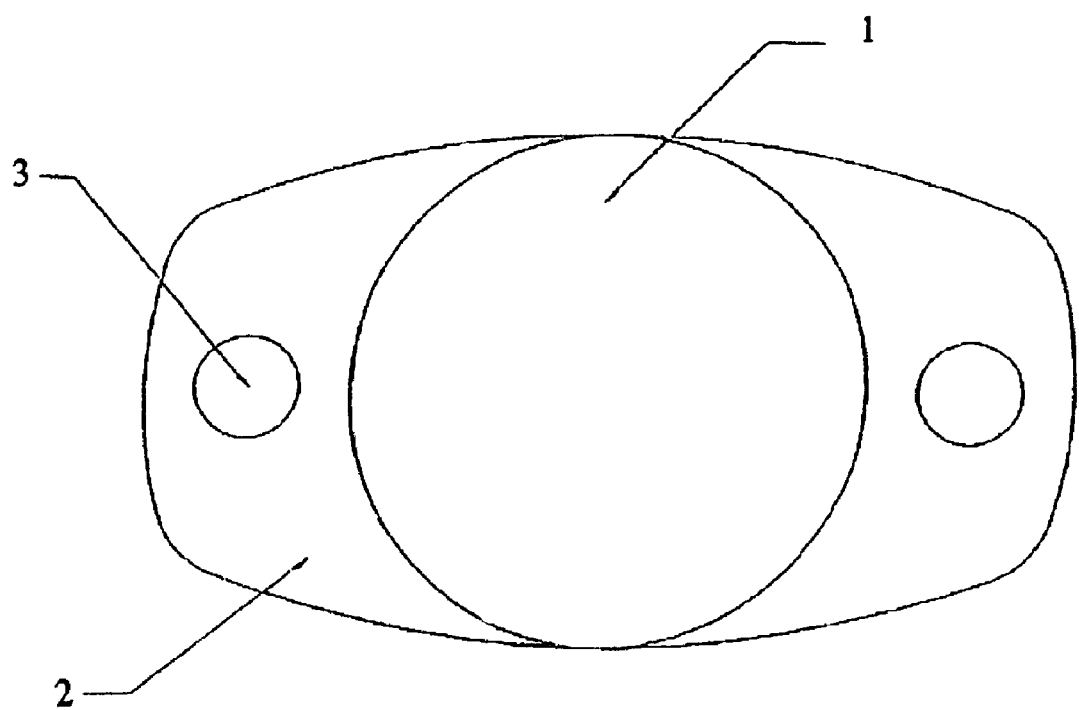
FIG. 1A is a top view of an intraocular lens having a plate-shaped haptic.
Figure 1B:
FIG. 1B is a side view of the intraocular lens having a plate-shaped haptic shown in FIG. 1A.
Figure 2A:
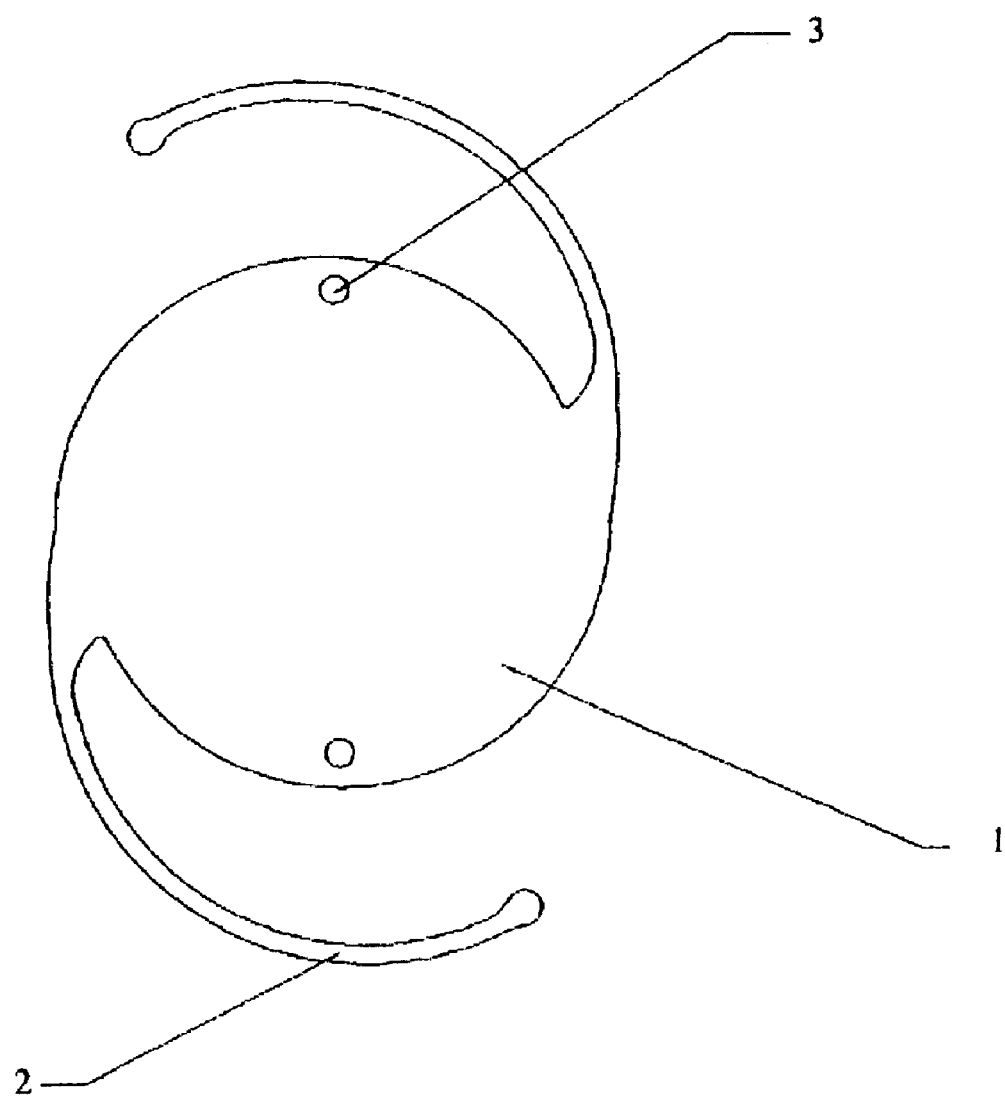
FIG. 2A is a top view of an intraocular lens having a C-shaped haptic.
Figure 2B:
FIG. 2B is a side view of the intraocular lens having a C-shaped haptic shown in FIG. 2A.
Figure 3A:
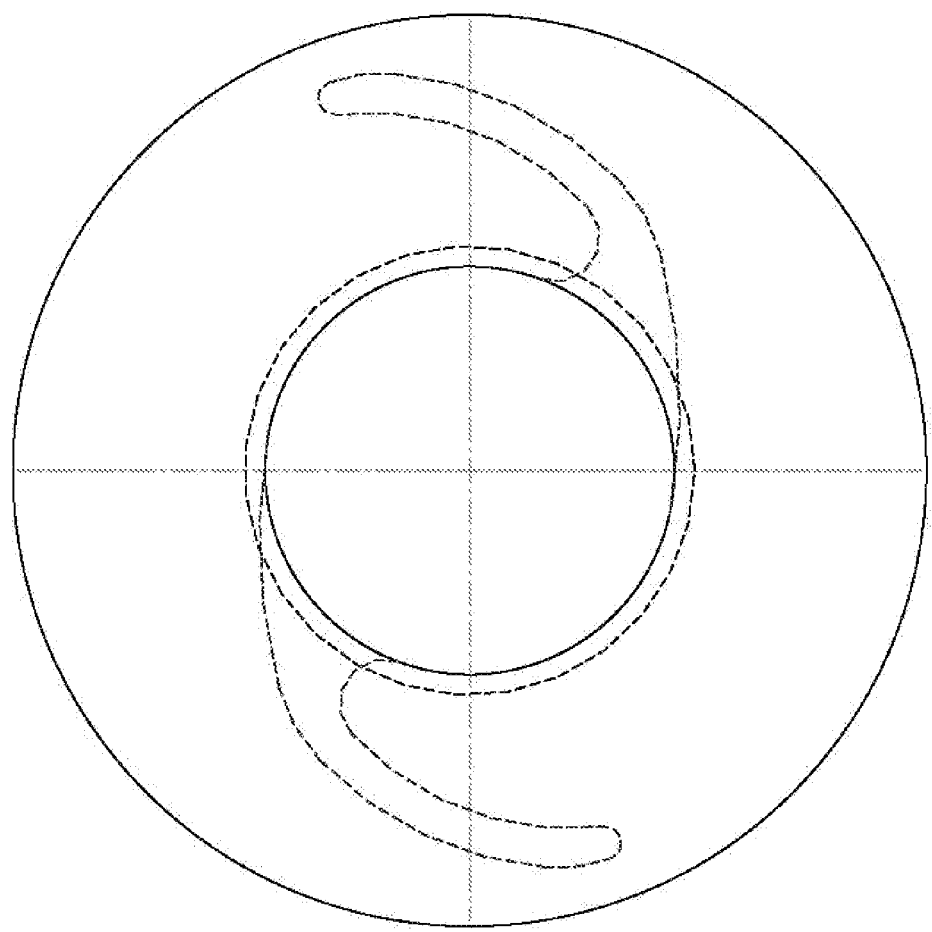
FIG. 3A is a top view of an intraocular lens universal blank.
Figure 3B:
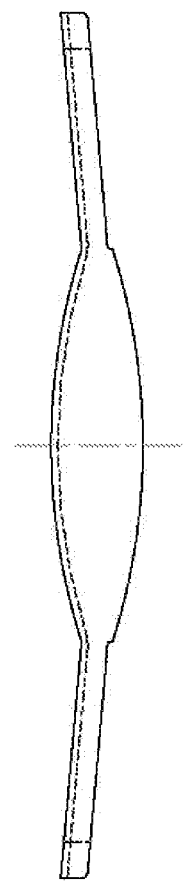
FIG. 3B is a side view of an intraocular lens universal blank shown in FIG. 3A.

All references cited herein are incorporated by reference in their entirety.

Intraocular lens are generally known in the art. See, for example, U.S. Pat. Nos. 7,947,796; 7,387,642; 7,067,602; 6,517,750; and 6,267,784.

One embodiment provides an intraocular lens comprising at least one copolymer comprising a series of monomeric subunits including, for example: (a) one or more first monomeric subunits comprising a polymerized acrylate or methacrylate group, at least one side group comprising (i) an aryloxy moiety, and (ii) an aliphatic carbon moiety linking the aryloxy moiety with the polymerized acrylate or methacrylate group, wherein the aliphatic carbon moiety comprises at least one hydroxyl substituent, and (b) one or more second monomeric subunits different from the first monomeric subunits comprising a polymerized acrylate or methacrylate group, and comprising at least one alkoxyalkyl side group, and (c) one or more third monomeric subunits different from the first and second monomeric subunits, the third monomeric subunits comprising a polymerized acrylate or methacrylate group, and comprising at least one alkylene oxide side group, wherein the first monomeric subunit is present in a greater amount by weight than the second monomeric subunit, and the first and second monomeric subunits together comprise about 75 percent or more of the monomeric subunits composition by weight.

First/Primary Monomeric Subunit

The first monomeric subunit can be the monomer subunit present in the largest amount as measured by weight percent for the copolymer. This subunit comprises a polymerizable moiety, such as acrylate, methacrylate, acrylamide and/or methacrylamide. The subunit also comprises an aliphatic spacer comprising one or more hydroxyl moieties. Finally, first monomeric subunit comprises an optionally substituted aryl or aryloxy moiety. In another embodiment, the one or more first monomeric subunits comprising a polymerized acrylate or methacrylate group may instead comprise a polymerized acrylamide or methacrylamide group that is optionally substituted at the nitrogen by hydrogen or a C1 to C5 alkyl.

For example, aryloxyalkyl methacrylate monomers can be represented by the formula Ar—O—$R_1$-MA where Ar is an optionally substituted aryl compound such as, for example, an optionally substituted phenyl, $R_1$ is an aliphatic spacer such as a bivalent alkyl group and "MA" is methacrylate. Alternatively, aryloxyalkyl acrylate monomers can be represented by the formula Ar—O—$R_2$-A where Ar is an optionally substituted aryl compound such as, for example an optionally substituted phenyl, $R_2$ is an aliphatic spacer such as a bivalent alkyl group and "A" is acrylate. Likewise, aryloxyalkyl acrylamide monomers can be represented by the formula Ar—O—$R_3$-AA where Ar is an optionally substituted aryl compound such as, for example, an optionally substituted phenyl, $R_3$ is an aliphatic spacer such as a bivalent alkyl group and "AA" is acrylamide. In addition, aryloxyalkyl methacrylamide monomers can be represented by the formula Ar—O—$R_4$-MAA where Ar is an optionally substituted aryl compound such as, for example, an optionally substituted phenyl, $R_4$ is an aliphatic spacer such as a bivalent alkyl group and "MAA" is methacrylamide. The bivalent group $R_1$, $R_2$, $R_3$, and $R_4$ may be further substituted by at least one hydroxy group. The AA or MAA monomers can be optionally substituted at the nitrogen by hydrogen or a C1 to C5 alkyl. Examples of C1 to C5 alkyl include methyl, ethyl, propyl, butyl, pentyl, and isomers thereof.

Both hydroxy-substituted aryloxyalkyl methacrylates and hydroxy-substituted aryloxyalkyl acrylates are ester-containing monomer compounds as will be recognized by those skilled in the art. Likewise, those skilled in the art would recognize hydroxy-substituted aryloxyalky acrylamides and hydroxy-substituted aryloxyalky methacrylamides as amide-containing monomer compounds. In some embodiments, $R_1$, $R_2$, $R_3$, and $R_4$ can be independently selected from hydroxy-substituted alkyl groups having 1 to 5 carbon atoms and in some embodiments 1, 2, 3, 4, or 5 carbon atoms, the alkyl group is substituted by one or more hydroxy groups. With respect to $R_1$, it will be understood that the hydroxy-substituted alkyl group is bonded to the O of the Ar—O group and is also bonded to the O atom of the MA group. Similarly, with respect to $R_2$, it will be understood that the hydroxy-substituted alkyl group is bonded to the O of the Ar—O group and is also bonded to the O atom of the A group. Similarly, with respect to $R_3$, it will be understood that the hydroxy-substituted alkyl group is bonded to the O of the Ar—O group and is also bonded to the N atom of the AA group. Similarly, with respect to $R_4$, it will be understood that the hydroxy-substituted alkyl group is bonded to the O of the Ar—O group and is also bonded to the N atom of the MAA group. The hydroxy group may be substituted to any carbon of the alkyl group. Hydroxy-substituted alkyl groups that may be used in accordance with the embodiments herein include straight chain alkyl groups, including but not limited to methyl, ethyl, propyl, butyl, and pentyl groups, wherein at least one C—H is substituted for C—OH. Alkyl groups may also include branched chain isomers of straight chain alkyl groups including, but not limited to, the following, which are provided by way of example only: —CH(CH$_3$)$_2$, —CH(CH$_3$)(CH$_2$CH$_3$), —CH(CH$_2$CH$_3$)$_2$, —C(CH$_3$)$_3$, and the like, wherein at least one C—H is substituted for C—OH. In some embodiments, the hydroxy-substituted aryloxyalkyl methacrylate or hydroxy-substituted aryloxyalkyl acrylate is selected where $R_1$ and $R_2$ have 1, 2, 3, or 4 carbon atoms. Specific embodiments of $R_1$, $R_2$, $R_3$, and $R_4$ are by way of non-limiting example 1-hydroxy propyl, 2-hydroxy propyl, 3-hydroxy propyl, 2-hydroxy butyl, 3-hydroxy butyl, 2,3-dihydroxy butyl and the like. The AA or MAA monomers being optionally substituted at the nitrogen by hydrogen or a C1 to C5 alkyl.

Aryloxy groups will be recognized by those skilled in the art to include an aryl compound bonded to oxygen atom. In some embodiments, the aryl group comprises optionally substituted phenyl or naphthyl. In some embodiments, the aryl group may comprise one or more heteroatoms, such as by way of non-limiting example nitrogen or sulfur. The aryl moiety may be optionally substituted by one or more alkyl groups including but not limited to methyl, ethyl, propyl, butyl, and pentyl groups. The alkyl groups may be branched chain isomers of straight chain alkyl groups. The aryl moiety may be optionally substituted by one or more alkoxy groups comprising an alkyl group bound to an oxygen, the alkyl group comprising, but not limited to methyl, ethyl, propyl, butyl, and/or pentyl groups. The alkyl groups may be branched chain isomers of straight chain alkyl groups. Additionally the aryl moiety may be substituted by one or more halogen groups, for example, F, Cl, Br, and/or I.

Examples of some specific hydroxy-substituted aryloxyalkyl methacrylate, hydroxy-substituted aryloxyalkyl acrylate, hydroxy-substituted aryloxyalkyl methacrylamide and hydroxy-substituted aryloxyalkyl acrylamide monomers useful for forming the copolymers, but are not limited to, 2-hydroxy-3-phenoxypropyl acrylate, 2-hydroxy-3-phenoxypropyl methacrylate, 2-hydroxy-3-phenoxypropyl acrylamide, and/or 2-hydroxy-3-phenoxypropyl methacrylamide.

In some embodiments, the present copolymers may also include a first monomer that is represented by the general formula (I), wherein R is hydrogen or methyl, Y is O or —NR", X is H, Cl, Br, —CH$_3$, or —OCH$_3$, n is 1 to 6, R" is hydrogen or a C1 to C5 alkyl.

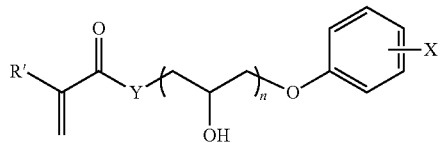

(I)

In other embodiments, n is 1 or 2 and X is hydrogen and Y is O.

Hence, one preferred embodiment provides an intraocular lens, wherein the first monomer subunits comprise a polymerized acrylate group. In another embodiment, the aryloxy group comprises a phenoxy group. In yet another embodiment, the aryloxy group comprises an unsubstituted phenoxy group. In another embodiment, the aliphatic carbon moiety of the first monomeric subunit is substituted with one hydroxyl group. In another embodiment, the aliphatic carbon moiety of the first monomeric subunit is a C3 moiety. In another embodiment, the aliphatic carbon moiety of the first monomeric subunit is represented by —CH$_2$—CHOH—CH$_2$—. Finally, the side group of the first monomeric subunit, in one embodiment, comprises —CH$_2$—CHOH—CH$_2$—OPh, wherein OPh is an unsubstituted phenoxy group.

Second Monomeric Subunit

The present copolymers may also include one or more hydrophobic monomeric subunits that can be formed from a second monomer different from the first monomer. Examples of such hydrophobic monomers used to make the monomeric subunits include alkoxyalkyl methacrylate and/or alkoxyalkyl acrylate monomers. Alkoxyalkyl methacrylate monomers can be represented by the formula $R_5$—O—$R_6$-MA where $R_5$ and $R_6$ are alkyl groups and "MA" is methacrylate. Alkoxyalkyl acrylate monomers can be represented by the formula $R_7$—O—$R_8$-A where $R_7$ and $R_8$ are alkyl groups and "A" is acrylate. Both alkoxyalkyl methacrylates and alkoxyalkyl acrylates are ester-containing monomer compounds as will be recognized by those skilled in the art. In some embodiments, $R_5$ to $R_8$ can be independently selected from alkyl groups having 1 to 5 carbon atoms and in some embodiments 1, 2, 3, 4, or 5 carbon atoms. With respect to $R_6$, it will be understood that the alkyl group is bonded to the O of the $R_5$—O group and is also bonded to the O atom of the MA group. Similarly, with respect to $R_8$, it will be understood that the alkyl group is bonded to the O of the $R_7$—O group and is also bonded to the O atom of the A group. Alkyl groups that may be used in accordance with the embodiments herein include straight chain alkyl groups, including but not limited to methyl, ethyl, propyl, butyl, and pentyl groups. Alkyl groups may also include branched chain isomers of straight chain alkyl groups including, but not limited to, the following, which are provided by way of example only: —CH(CH$_3$)$_2$, —CH(CH$_3$)(CH$_2$CH$_3$), —CH(CH$_2$CH$_3$)$_2$, —C(CH$_3$)$_3$, and the like. In some embodiments, the alkoxyalkyl methacrylate or alkoxyalkyl acrylate is selected where $R_5$, to $R_8$ have 1, 2, 3, or 4 carbon atoms. Examples of some specific alkoxyalkyl methacrylate and alkoxyalkyl acrylate monomers useful for forming the copolymers of the embodiments herein include, but are not limited to, methoxyethyl methacrylate, ethoxyethyl methacrylate, propoxyethyl methacrylate, butoxymethyl methacrylate, methoxypropyl methacrylate, ethoxypropyl methacrylate, propoxypropyl methacrylate, butoxypropyl methacrylate, methoxybutyl methacrylate, ethoxybutyl methacrylate, propoxybutyl methacrylate, butoxybutyl methacrylate, methoxyethyl acrylate, ethoxyethyl acrylate, propoxyethyl acrylate, butoxymethyl acrylate, methoxypropyl acrylate, ethoxypropyl acrylate, propoxypropyl acrylate, butoxypropyl acrylate, methoxybutyl acrylate, ethoxybutyl acrylate, propoxybutyl acrylate, and butoxybutyl acrylate. In some preferred embodiments, the copolymer includes ethoxyethyl methacrylate (EOEMA).

Hence, a particularly preferred embodiment provides an intraocular lens, wherein the alkoxyalkyl group is a C3 to C12 group. In one embodiment, the alkoxyalkyl group comprises a single oxygen atom. In a specific embodiment, the alkoxyalkyl group is 2-ethoxyethyl.

In some embodiments, a hydrophobic monomer that is not referenced above, but known to be a monomer suitable for foldable IOLs may be incorporated. Examples of an additional hydrophobic monomer include, but are not limited to, alkoxyalkoxyalkyl methacrylates such as, but not limited to, ethoxyethoxyethyl methacrylate; alkoxyalkoxyalkyl acrylates, such as, but not limited to ethoxyethoxyethyl acrylate; alkyl methacrylate monomers; and combinations thereof with specific examples of alkyl methacrylate monomers being $C_1$ alkyl to $C_{15}$ alkyl methacrylate monomers such as, but not limited to, methyl methacrylate, ethyl methacrylate, propyl methacrylate, butyl methacrylate, hexyl methacrylate, lauryl methacrylate, and combinations thereof.

Third Monomeric Subunit

A third monomeric subunit can be present which is different from the first and second monomeric subunits. The present copolymers may also include, for example, one or more polyalkylene glycol alkylether acrylate and/or polyalkylene glycol alkylether methacrylate monomers including of higher molecular weight. Examples of polyalkylene glycol alkylether acrylate and/or polyalkylene glycol alkylether methacrylate include, for example, polyethylene glycol monomethyl ether methacrylate monomers of varying molecular weight. In some embodiments, the third monomer may be polyethylene glycol monomethyl ether methacrylate (200 PEG MW) or polyethylene glycol monomethyl ether methacrylate (400 PEG MW). In another embodiment, polyethylene glycol monomethyl ether methacrylate of other molecular weights may be used. Other polyethylene glycol monomethyl ether methacrylate compositions may be used.

Hence, a particularly preferred embodiment provides an intraocular lens or IOL blank, wherein the alkyleneoxide side group is a poly(alkyleneoxide) side group. In one embodiment, the alkyleneoxide side group has a molecular weight of 100 g/mol to 2,000 g/mol. In another embodiment, the alkyleneoxide side group has a molecular weight of 100 g/mol to 1,000 g/mol. In yet another embodiment, the alkyleneoxide side group has a molecular weight of 100 g/mol to 500 g/mol. In one embodiment, the alkyleneoxide side group is a poly (ethyleneoxide) side group. In one embodiment, the third monomeric subunit consists of polymerized polyethylene glycol monomethyl ether methacrylate with a polyethylene glycol molecular weight of about 150 to 250. In another embodiment, the third monomeric subunit consists of polymerized polyethylene glycol monomethyl ether methacrylate with a polyethylene glycol molecular weight of about 350 to 450.

Crosslinker (Fourth Monomer)

The intraocular lens can comprise a copolymer that further comprises fourth monomeric subunits that are crosslinked subunits. In particular, trifunctional crosslinking agents can be used to form the crosslinked subunits. However, other di- or multi functional crosslinking agents known in the art may also be employed.

The copolymers can be prepared using conventional polymerization techniques known to those in the field of polymer chemistry. Crosslinkers may be employed in the polymerization reaction. For example, any crosslinking or difunctional monomer, can be used in effective amounts to give the desired crosslinking density. For example, in a concentration range of 0 to about 10 percent, such as about 0.01 to about 4 percent, or in some embodiments from 0.5 to 3 percent by weight, based on the weight of the polymer. Examples of suitable crosslinking agents include di-olefinic functional component or ethylene glycol dimethacrylate (EGDMA). Generally, crosslinkers help to enhance the resulting copolymer's dimensional stability.

In some embodiments, the compositions include one or more crosslinker with three or more polymerizable functionalities (a multi-functional crosslinking agent). An example of a multi-functional crosslinking agent includes, but is not limited to, trimethylol propane trimethacrylate (TMPTMA). The analogous acrylate crosslinking agents, for example, trimethylol propane triacrylate, may also be utilized in place of any of their methacrylate analogs or in combination with the methacrylate analogs. Some embodiments include two or more trifunctional crosslinking agents or a multi-functional crosslinking agent and a di-functional crosslinking agent known in the art or incorporated herein by reference, such as for example EGDMA. Therefore, in some embodiments, the copolymer compositions include EGDMA and TMPTMA. In some such embodiments, the amount of EGDMA ranges from about 0.05 to about 0.5 or about 0.4 percent by weight based on the weight of the dry copolymer and the amount of the TMPTMA ranges from about 0.3 to about 1.5 percent by weight based on the weight of the dry polymer. In some such embodiments, the amount of EGDMA ranges from about 0.08 to about 0.25 percent by weight based on the weight of the dry copolymer and the amount of the TMPTMA ranges from about 0.45 to about 1.2 percent by weight based on the weight of the dry polymer. In still other such embodiments, the amount of EGDMA ranges from about 0.1 to about 0.2 percent by weight based on the weight of the dry copolymer and the amount of the TMPTMA ranges from about 0.5 to about 1.0 percent by weight based on the weight of the dry polymer.

In one embodiment, the only crosslinker used is a trifunctional crosslinker such as a trifunctional methacrylate crosslinker.

Examples of specific copolymers useful in the present embodiments are discussed in the examples where all weights are shown in grams.

Compositions/Amounts

The copolymers described herein can include the first monomers e.g. the hydroxy-substituted aryloxyalkyl methacrylate or hydroxy-substituted aryloxyalkyl acrylate monomers as the major component and the second and third monomers as the minor component, measured by weight.

In the present copolymers, the total quantity of the one or more of the first monomer can make up the majority of the polymer, as measured by weight. For example, in some embodiments, the total quantity of the combined amounts of any hydroxy-substituted aryloxyalkyl methacrylate, hydroxy-substituted aryloxyalkyl acrylate, hydroxy-substituted aryloxyalkyl meth acrylamide or hydroxy-substituted aryloxyalkyl acrylamide monomer may be about 50 percent to about 80 percent by weight based on the total weight of the polymer. Alternately, the first monomer may comprise about 60 percent to about 65 percent by weight of the polymer. While the present claims are not limited by theory, the presence of the hydroxy-substituted aryloxyalkyl moiety may provide a hydrophobic copolymer subject to less glistening based on the hydroxyl functionality, which can provide a hydrogen bond donor/acceptor site to increase compatibility with the water.

In the present copolymers, the total quantity of the one or more of the second monomer will make up a minority of the polymer, as measured by weight. For example, in some embodiments, the total quantity of the combined amounts of second monomer may be about 20 percent to about 35 percent by weight of the total weight of the polymer. Alternately, the second monomer may comprise from about 27 percent to about 32 percent by weight of the polymer. The second monomer is a hydrophobic monomer providing a low glass transition temperature, such as for example EEOMA.

In the present copolymers, the total quantity of the one or more of the third monomer will make up a minority of the polymer. For example, in some embodiments, the total quantity of the combined amounts of third monomer may be about 5 percent to about 15 percent by weight of the polymer. Alternately, the third monomer may comprise about 7 percent to about 10 percent by weight of the polymer. The third monomer has a higher molecular weight and therefore can provide reduction of glistening by use of a smaller number of molecules while also not substantially increasing the $T_g$ of the final polymeric material.

In the present copolymers, the total quantity of the one or more of the crosslinking monomer will make up a minority of the polymer. For example, in some embodiments, the total quantity of the combined amounts of incorporated crosslinking monomer ranges from 0.3 percent to 1.5 percent, and in some embodiments from 0.45 percent to 1.2 percent or from 0.5 to 1.0 percent, based on the total weight of the dry copolymer of the optic portion.

When a polymer or copolymer is said to include or contain a monomer such as ethoxyethyl methacrylate, it will be understood that this means that the ethoxyethyl methacrylate monomer has been reacted and incorporated into the polymer. A monomer of the claimed compounds may also be in the form of an oligomer that can be polymerized into the embodied copolymeric compounds.

One exemplary polymeric composition contains about 50 percent to about 70 percent of a polymerized hydroxy-substituted aryloxyalkyl methacrylate and/or polymerized hydroxy-substituted aryloxyalkyl acrylate, about 20 percent to about 35 percent of a polymerized alkoxyalkyl methacrylate and/or polymerized alkoxyalkyl acrylate and about 5 percent to about 15 percent of a polymerized polyethylene glycol monomethyl ether methacrylate, with the balance of the copolymer being made up of other components, such as UV absorbers, initiation agents and/or crosslinking agents. Another exemplary composition contains about 60 percent to about 65 percent of a polymerized hydroxy-substituted aryloxyalkyl methacrylate and/or polymerized hydroxy-substituted aryloxyalkyl acrylate, about 27 percent to about 32 percent of a polymerized alkoxyalkyl methacrylate and/or polymerized alkoxyalkyl acrylate and about 7 percent to about 10 percent of a polymerized polyethylene glycol monomethyl ether methacrylate, with the balance of the copolymer again being made up of other components. Another exemplary composition contains about 65 percent to about 70 percent of a polymerized hydroxy-substituted aryloxyalkyl methacrylate and/or polymerized hydroxy-substituted aryloxyalkyl acrylate, about 20 percent to about 30 percent of a polymerized alkoxyalkyl methacrylate and/or polymerized alkoxyalkyl acrylate and about 5 percent to about 15 percent of a polymerized polyethylene glycol monomethyl ether methacrylate, with the balance of the copolymer again being made up of other components. Another exemplary composition contains about 50 percent to about 70 percent of polymerized 2-hydroxy-3-phenoxypropyl acrylate, about 20 percent to about 35 percent of a polymerized alkoxyalkyl methacrylate and/or polymerized alkoxyalkyl acrylate and about 5 percent to about 15 percent of a polymerized polyethylene glycol monomethyl ether methacrylate, with the balance of the copolymer again being made up of other components. In some of these compositions, the polymerized hydroxy-substituted aryloxyalkyl acrylate and/or polymerized hydroxy-substituted aryloxyalkyl methacrylate may be polymerized 2-hydroxy-3-phenoxypropyl acrylate. In still other such compositions, the polymerized alkoxyalkyl methacrylate and/or polymerized alkoxyalkyl acrylate is polymerized 2-ethoxyethyl methacrylate. In still other such compositions, the polymerized polyethylene glycol monomethyl ether methacrylate monomer has a molecular weight from about 200 to about 400. As can be seen from these exemplary compositions, the present intraocular lens can have a range of material components and still have the desired characteristics.

In another embodiment, the compositions of the preceding paragraph comprise polymerized hydroxy-substituted aryloxyalkyl methacrylamide and/or polymerized hydroxy-substituted aryloxyalkyl acrylamide as a first monomer in place of the polymerized hydroxy-substituted aryloxyalkyl methacrylate and/or polymerized hydroxy-substituted aryloxyalkyl acrylate.

In some of embodiments, the copolymer compositions of the present embodiments consist of or consist essentially of a copolymer formed from a hydroxy-substituted aryloxyalkyl acrylate, an alkoxyalkyl methacrylate, polyalkylene glycol alkylether methacrylate and one or more crosslinking agent.

In some such embodiments, the copolymer is formed from a monomers consisting of 2-hydroxy-3-phenoxypropyl acrylate, 2-ethoxyethyl methacrylate, polyethylene glycol monomethyl ether methacrylate, and TMPTMA.

In some embodiments, a copolymer comprises, consists essentially of, or consists of:

(a) An incorporated hydroxy-substituted aryloxyalkyl acrylate such as 2-hydroxy-3-phenoxypropyl acrylate in an amount of from 50 to 80 percent;

(b) An incorporated alkoxyalkyl methacrylate and/or alkoxyalkyl acrylate such as 2-ethoxyethyl methacrylate in an amount of from 20 to 35 percent;

(c) An incorporated polyethylene glycol monomethyl ether methacrylate such as PEG200M or PEG400M in an amount of from 5 to 15 percent;

(d) An incorporated functional methacrylate or acrylate crosslinking agent such as TMPTMA in an amount ranging from 0.4 to 1 percent; and (e) optionally, one or more optional other ingredients such as water, one or more UV absorbing compound or monomer, a colorant, and an antioxidant.

In an embodiment, the first and second monomeric subunits together comprise about 70, 75, 80, 85 and/or 90 percent or more of the monomeric subunits composition by weight.

Properties of Composition

The copolymers can have a water content of less than or about 5 percent, or less than about 3 percent, based on the weight of the copolymer after it is fully equilibrated in water. In some embodiments, the copolymers have a water content at equilibrium that ranges from at or about 1 percent to at or about 5 percent based on the weight of the copolymer after it is fully equilibrated in water. In other embodiments, the water content ranges from about 2 percent to about 4 percent by weight of the copolymer after it is fully equilibrated with water.

The copolymers can possess superior mechanical and optical properties over other materials used to make IOLs. Often, because hydrophobic IOLs are incompatible with water, they form glistenings caused by water droplets in the material's voids. It is applicant's belief that the hydroxyl functionality adjacent to the aryloxy functionality can provide a hydrogen bond donor/acceptor site to increase compatibility with the water. The combination of a monomer such as a hydroxy-substituted aryloxyalkyl acrylate with a hydrophobic monomer such as an alkoxyalkyl methacrylate with a low $T_g$ can provide materials with increased refractive index over the prior art, which also remain foldable. Furthermore, the additional of PEG 200 or PEG 400 can provide hydrogen-bond acceptors that also can provide a plasticization effect so the $T_g$ remains low. The components of present embodiments can provide for a hydrophobic lens with low $T_g$, reduced glistenings and reduced stickiness providing for an IOL with desirable and reliable unfolding times, while maintaining a high refractive index.

The copolymers can be designed to have a wide range of physical characteristics. In some instances, the present copolymers can be designed to have glass transition temperatures below at or about 35° C., below at or about 30° C., below at or about 25° C., such as from at or about −25° C. to at or about 35° C., 30° C., or 25° C., from about −5° C. to about 5° C., 10° C., 15° C., 20° C., or about 25° C. or from at or about 0° C. to at or about 15° C. In preferred embodiments, the glass transition temperature will be from about −5° C. to about 5° C. Glass transition temperatures referred to herein may be measured at half width at a temperature change rate of 10° C./minute, or other methods known in the art. As the present copolymers have been designed to be used as intraocular lenses, they also typically have a high refractive index, which is generally above about 1.40. Some of the present copolymers can have a refractive index of 1.48 or higher. Some of the present copolymers can have a refractive index of 1.50 or higher. Because the present copolymers are hydrophobic, they can also have equilibrium water contents that are about 5 percent or less, for example 4 percent, 3 percent, 2 percent, 1 percent or less. Due to their low water contents, the present copolymers are generally not considered hydrogels and may be considered as hydrophobic. Generally, the present lenses also have advantageous properties compared to prior lenses because they have a comparable or higher refractive index than lenses containing silicone or p-hydroxyethyl methacrylate and are more flexible, e.g., foldable, than hydrophobic lenses that include aromatic monomers to increase the refractive index of the resulting polymer.

Lens

A present embodiment also provides intraocular lenses made at least partially from the present copolymers. Such intraocular lenses include an optic portion and one or more haptic portions. Typically, the copolymers of the embodiments will make up part or the entire optic portion of the intraocular lens. In some embodiments, the optic portion of the lens will have a core made from one of the present copolymer surrounded by different polymer or material. Lenses in which the optic portion is made up of at least partially of one of the present copolymers will usually also have a haptic portion. The haptic portion can also be made of copolymer of the embodiments or can be made of a different material, for example another polymer.

In some embodiments, the present intraocular lens is a one-piece lens having a soft, foldable central optic region and an outer peripheral region (haptic-region) in which both regions are made of the same polymer. In other embodiments, the optic and haptic regions can be formed from different types of polymers or materials, if desired. Some lenses can also have haptic portions that are made up of different materials, for example where one or more haptic portions is made from the same material as the optic portion and other haptic portions are made of materials other than a polymer of the embodiments. Multicomponent lenses can be made by embedding one material in the other, concurrent extrusion processes, solidifying the hard material about the soft material, or forming an interpenetrating network of the rigid component into a preformed hydrophobic core. In instances where one or more haptic portions are made from a different material than the optic portion of the lens, the haptic portion can be attached to the optic portion in any manner known in the art, such as by drilling a hole or holes in the optic portion and inserting the haptic portion.

The copolymers of the present embodiments can be designed so that they are capable of being folded so that the intraocular lens can be inserted into the eye of an individual through a small incision. The haptic portion of the lens provides the required support for the lens in the eye after insertion and unfolding of the lens and tends to help stabilize the position of the lens after insertion and the closure of the incision. The shape of the haptic portion design is not particularly limited and can be any desired configuration, for example, either a plate type or graduated thickness spiral filaments, also known as a C-loop design.

FIGS. 1A, 1B, 2A, 2B, 3A, and 3B illustrate examples of intraocular lenses in accordance with the present embodiments. The figures are for illustrative purposes only and do not limit the scope of the embodiments. For instance, the intraocular lens can be any type of intraocular lens. In the FIGS. 1 and 2, 1 is the optic portion of the lens, 2 is the haptic portion, and 3 is a positioning hole. FIG. 3 provides a universal blank that provides a lens shaped out of the mold, and requires only minimal cutting and/or shaping from the molded polymer to be a finished IOL. One skilled in the art of intraocular lenses understands the functions of these portions of the intraocular lens.

The optic portion 1 can be approximately 6 mm in diameter prior to hydration. The 6 mm diameter is fairly standard in the art, and is generally chosen to cover the pupil in its fully dilated state under naturally occurring conditions. However, other sizes are possible and the present embodiments are not limited to any particular diameter or size of intraocular lens. Furthermore, it is not necessary that the lens optic portion be circular; it could also be oval, square, or any other shape as desired.

The intraocular lens can further include one or more non-optical haptic components 2 extending away from the outermost peripheral surface of the optic portion. The haptic components can be of any desired shape, for example, graduated spiral filaments or flat plate sections and are used to support the lens within the posterior chamber of the eye. Lenses having any desired design configuration can be fabricated. Further, although two types of haptic designs are shown in the figures, the haptics can have configurations other than those illustrated. Should the intraocular lens include other components besides the optical and haptic portions, such other portions can be made of a polymer as are the haptic and optic portions, or if desired, another material.

The intraocular lenses of the embodiments may be inserted into the eye in known manners. For example, the intraocular lens may be folded prior to insertion into the eye by small, thin forceps of the type typically used by ophthalmic surgeons. After the lens is in the targeted location, it is released to unfold. As is well known in the art, typically the lens that is to be replaced is removed prior to insertion of the intraocular lens. The intraocular lens of the present embodiments can be made of a generally physiologically inert soft polymeric material that is capable of providing a clear, transparent, refractive lens body even after folding and unfolding. In some embodiments, the foldable intraocular lens of the present embodiments can be inserted into any eye by injection whereby the mechanically compliant material is folded and forced through a small tube such as a 1 mm to 3 mm inner diameter tube. In one embodiment the small tube has an inner diameter of approximately 2.0 or 1.9 or 1.8 or 1.7 or 1.6 or 1.5 mm or less. In one embodiment the inner diameter is approximately 1.4 to 2.0 mm. In one embodiment, the inner diameter is approximately 1.8 mm, in another it is 1.6 mm. In one embodiment, the finished IOL lens is microinjectable (e.g. able to be injected through a small tube that has an inner diameter of approximately 1.8 mm or 1.6 mm).

Methods of Making Composition

The copolymers of the embodiments herein can be prepared using conventional polymerization techniques known to those in the field of polymer chemistry. Crosslinkers, also referred to as crosslinking agents, may be employed in the polymerization reaction. For example, any suitable crosslinking di-functional, multi-functional monomer, or combination of these can be used in effective amounts to give the desired crosslinking density. For example, in a concentration range of 0.4 to about 4 percent, such as about 0.4 to about 3 percent, or in some embodiments from 0.5 to 1.5 percent by weight, based on the weight of the polymer. Examples of suitable crosslinking agents include di-olefinic compounds such as ethylene glycol dimethacrylate (EGDMA) and tetraethylene glycol dimethacrylate (TEGDMA) and other cross-linking agents such as trimethylol propane trimethacrylate (TMPTMA) which include three or more olefinic polymerizable functionalities. Generally, crosslinkers help to enhance the resulting polymer's dimensional stability.

Also, if desired an initiator can be used in the polymerization. Any initiator commonly used in the art, such as azo derivatives, like 2,2-azobis(2,4-dimethylvaleronitrile) and propanenitrile,2-methyl,2,2'-azobis, can be used. The initiator may also be a UV initiator or other type of imitator as recognized by one skilled in the art. The initiator is used in an amount effective for initiation purposes, and is generally present from about 0.01 to 1.0 percent by weight, based on the weight of the polymer.

The copolymers of the present embodiments can also include additional monomers, such as, but not limited to, monomers that impart ultraviolet (UV) absorption to the polymer. UV absorbing monomers are typically aromatic compounds with olefinic functionality. The advantageous UV absorbing compounds can be added prior to polymerization for incorporation into the resultant polymer, as is well known in the art. The UV absorber should preferably be capable of polymerization into the lens matrix so as to be stable under physiological conditions. Any monomer copolymerizable with the described monomers can optionally be used, so long as such monomer does not materially or adversely effect the basic characteristics of the intraocular lens. Examples of useful additional monomers that can used are described in U.S. Pat. No. 5,326,506, hereby incorporated by reference, directed to a composite intraocular lens. Additionally, aryl-substituted triazole compounds, such as for example, tris-aryl triazole compounds described in U.S. Pat. No. 6,365,652, may be used in at low concentrations to achieve desired UV absorbing properties. Such optional additional monomers, preferably are present in a total amount of not more than 10 weight percent, generally less than 5 weight percent, based on the total weight of the polymer.

As described above, it may be useful to add crosslinking agents such as EGDMA, TEGDMA, or TMPTA, for example, to enhance the resulting polymer's dimensional stability. It may also be advantageous to add UV absorbing compounds with the lens monomers prior to polymerization for incorporation into the resultant polymer. The UV absorber should preferably be capable of polymerization into the lens matrix so as to resist extraction under physiologic conditions. The UV-absorbing monomer can be present in an amount effective to give the desired UV-absorbing properties, generally less than 4 percent by weight of the polymer, such as from 0.01 to about 1 percent by weight of the polymer.

Examples of specific copolymers useful in the present embodiments are included in Table 1 which are also discussed in the examples where all weights used in the polymerization are shown in grams with the percentage of the monomers in the polymer shown in parenthesis based on the total of all monomers and crosslinking agents and assuming incorporation of all monomers and crosslinkers in the copolymers.

Formation of Intraocular Lens

The intraocular lenses of the present embodiments may be formed by methods known in the art. For example, in an exemplary process, the monomers that form the copolymer are polymerized into a polymer rod, polymer blanks or discs are formed from the rod, and then the blanks are cut, for example, by a lathe into the intraocular lens. The rods can be made by a procedure which begins with polymerizing, in a mold, such as in a tubular or cylindrical mold, a mixture of initiator and monomers, to form an optically clear soft lens body. As discussed above, it may be desirable to incorporate cross-linking materials and ultraviolet-absorbing compounds during polymerization or into the resultant polymer matrix. In some embodiments, the polymer rods are then cut and ground or otherwise machined, into blanks of the desired diameter and thickness by lathe cutting and machine milled at temperatures below the $T_g$ into an intraocular lens.

Generally, the composite material rod is lathe cut or ground to a diameter 0.5 to 2.0 mm thicker than the required distance from the center of the lens body to the furthest edge of the legs or haptics. This rod is then cut into blanks of uniform thickness. The blanks are ground and lapped to a diameter and thickness suitable for lathe cutting and machine milling in the conventional manner into the intraocular lens of the present embodiments. Because the present copolymers may have low glass transition temperatures, the rod or blanks may require cooling below $T_g$ prior to and/or during cutting, lathing and/or milling.

A general description of a stepwise process for forming the blanks into intraocular lenses is set forth in the flow chart below. One having ordinary skill in the field of intraocular lens manufacturing, from a review of the present specification, can make intraocular lenses using the general knowledge in the art on intraocular lens manufacture and the process of cryogenic machining Intraocular lenses can also be made by molding the present copolymer to form all or part of the optic portion of the lens. For example, the present copolymer can be polymerized in a mold by a liquid mixture of monomers and additional components, to form an optically clear soft lens body. These molding methods can involve molding the optics on one half of the lens, such as the anterior or posterior portion, or fully molding the lens. When only half of the optic portion of the lens is formed in the mold then the second side optics can be machined, for example as discussed above. In either of these embodiments, additional material can be molded to allow machining of various haptic designs. The copolymer may be optionally molded in the form of a preformed lens as known in the art as a universal blank.

Polymer does not Comprise Components

In one embodiment, the copolymer composition does not comprise a third monomer which is a hydrophilic, low molecular weight monomer having a molecular weight of less than about 150 g/mol, or less than about 100 g/mol.

For example, in one embodiment, the copolymer composition does not comprise polymerized hydroxyethylacrylate (HEA). In one embodiment, the copolymer composition does not comprise polymerized glycidyl methacrylate (GMA). In one embodiment, the copolymer composition does not comprise the combination of HEA and GMA.

Applications

One application is lens, including lens adapted for the human eye, including IOLs.

Additional embodiments are provided in the following non-limiting working examples and contrasted with comparative examples.

WORKING EXAMPLES

HPPA refers to 2-hydroxy-3-phenoxypropyl acrylate
EOEMA refers to 2-ethoxyethyl methacrylate
PEG200M refers to polyethylene glycol monomethyl ether methacrylate (200 PEG MW)
PEG400M refers to polyethylene glycol monomethyl ether methacrylate (400 PEG MW)
TMPTMA refers to trimethylol propane trimethacrylate Example 1

24.8 grams of HPPA were mixed with 12.2 grams of EOEMA, 3.0 grams of PEG200M, and 1.1 grams of TMPTMA. The mixture was degassed while applying vigorous stirring. The mixture was dispensed into molds and polymerized at 70° C. for eight hours, and post-cured at 95° C. for 10 hours. The molds were allowed to cool to room temperature. The molds were opened and the polymer disc was removed and inspected. The polymer displayed properties summarized in Table 1.

Example 2

26.0 grams of HPPA were mixed with 11.0 grams of EOEMA, 3.0 grams of PEG200M, and 1.1 grams of TMPTMA. The mixture was degassed while applying vigorous stirring. The mixture was dispensed into molds, polymerized at 70° C. for eight hours, and post-cured at 95° C. for 10 hours. The molds were allowed to cool to room temperature. The molds were opened and the polymer disc was removed and inspected. The polymer displayed properties summarized in Table 1.

Example 3

26.0 grams of HPPA were mixed with 10.0 grams of EOEMA, 4.0 grams of PEG200M, and 1.1 grams of TMPTMA. The mixture was degassed while applying vigorous stirring. The mixture was dispensed into molds, polymerized at 70° C. for eight hours, and post-cured at 95° C. for 10 hours. The molds were allowed to cool to room temperature. The molds were opened and the polymer disc was removed and inspected. The polymer displayed properties summarized in Table 1.

Example 4

24.8 grams of HPPA were mixed with 9.2 grams of EOEMA, 6.0 grams of PEG200M, and 1.1 grams of TMPTMA. The mixture was degassed while applying vigorous stirring. The mixture was dispensed into molds, polymerized at 70° C. for eight hours, and post-cured at 95° C. for 10 hours. The molds were allowed to cool to room temperature. The molds were opened and the polymer disc was removed and inspected. The polymer displayed properties summarized in Table 1.

Example 5

24.8 grams of HPPA were mixed with 9.2 grams of EOEMA, 6.0 grams of PEG400M, and 1.1 grams of TMPTMA. The mixture was degassed while applying vigorous stirring. The mixture was dispensed into molds, polymerized at 70° C. for eight hours, and post-cured at 95° C. for 10 hours. The molds were allowed to cool to room temperature. The molds were opened and the polymer disc was removed and inspected. The polymer displayed properties summarized in Table 1.

TABLE 1

Properties of Working Examples

| Example | Refractive Index at 20° C. | Refractive Index at 35° C. | Water Content (%) | $T_g$ (° C.) | Opening Time at 20° C. (s) | Opening Time at 35° C. (s) | Severity Index |
|---|---|---|---|---|---|---|---|
| 1 | 1.5200 | 1.5140 | 3.6 | 5 | 12 | 5 | 694 |
| 2 | 1.5190 | 1.5140 | 3.6 | 5 | 12 | 5 | 701 |
| 3 | 1.5180 | 1.5130 | 3.8 | 3 | 12 | 5 | 698 |
| 4 | 1.5180 | 1.5130 | 3.8 | 0 | 10 | 3 | 685 |
| 5 | 1.5080 | 1.5050 | 4.8 | −2 | 10 | 3 | 735 |

Example 5

Shear Force Measurements

Figure 4:
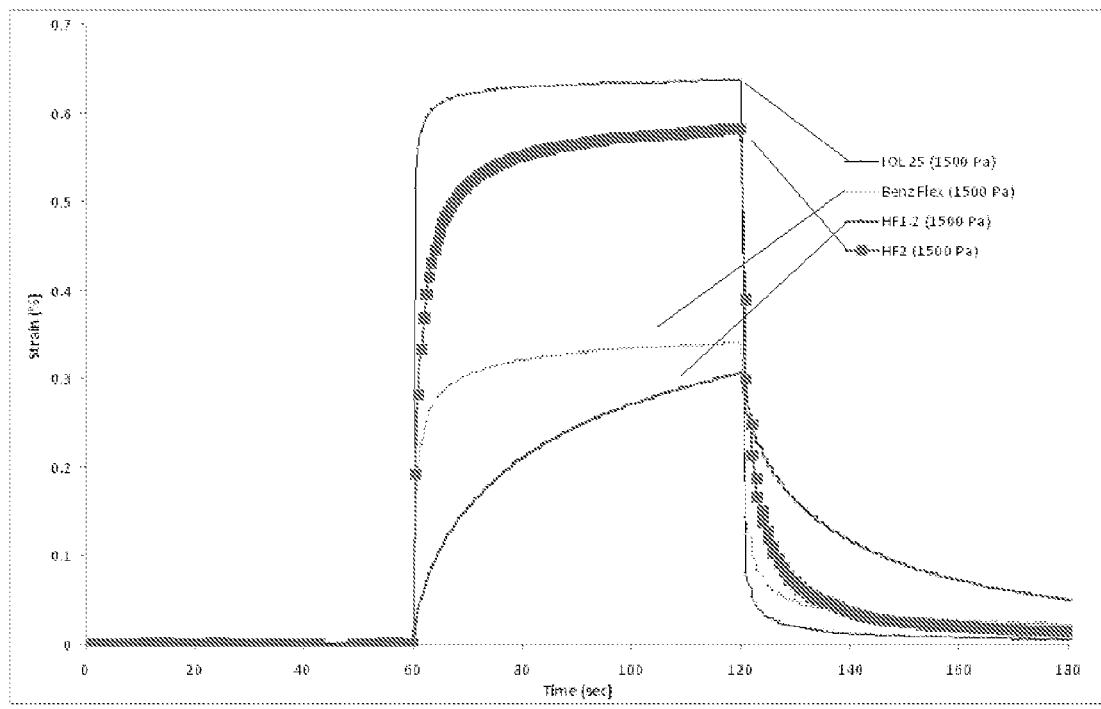
FIG. 4 shows the stress relaxation of several hydrophilic and hydrophobic IOL materials (25° C.) at 1500 Pa, including an embodiment of the present invention as HF2.

Using a precision Rheometer with a thermostat liquid cell maintained at 25° C., two commonly used hydrophilic IOL materials (Hydrophilic HEMA/EOEMA copolymer "IOL 25" (water content=25%) Hydrophilic HEMA/MMA copolymer and "Benz Flex" (water content=26%)) were examined. 1500 Pa of shear force was applied for 60 seconds at a normal holding force of 5 Newtons. The results are summarized in FIG. 4. The data shows that the IOL 25 material can absorb more than twice the shear force (through elastic deformation) and release it more quickly than the Benz Flex material. A commonly used Hydrophobic IOL material of (Hydrophobic EOEMA based copolymer "HF1.2" (Tg=4°

C.)) was subjected to similar conditions and can only absorb half the force and relaxes more slowly. HF1.2 is injectable through a 2.4-2.8 mm syringe and has an opening time of approximately 25-30 seconds. The ability to recover from deformation is affected by these properties. The Hydrophobic aromatic copolymer embodied herein, such as the IOL material of Example 1 ("HF2" (Tg=5° C.)) more closely resembles IOL 25 and releases nearly as quickly (see FIG. 4).

COMPARATIVE EXAMPLES

HPPA refers to 2-hydroxy-3-phenoxypropyl acrylate
EOEMA refers to 2-ethoxyethyl methacrylate
EOEA refers to 2-ethoxyethyl acrylate
TMPTMA refers to trimethylol propane trimethacrylate
HEA refers to 2-hydroxyethyl acrylate
GMA refers to glycerol methacrylate
SI refers to glistening Trattler severity index.

Comparative Example 1

24.8 grams of HPPA were mixed with 12.4 grams of EOEMA, 2.8 grams of HEA, and 1.1 grams of TMPTMA. The mixture was degassed while applying vigorous stirring. The mixture was dispensed into molds and polymerized at 70° C. for eight hours, and post-cured at 95° C. for 10 hours. The molds were allowed to cool to room temperature. The molds were opened and the polymer disc was removed and inspected. The polymer displayed a glistening level of SI=862 on the Trattler Severity Index.

Comparative Example 2

30.0 grams of HPPA were mixed with 7.0 grams of EOEA, 2.0 grams of HEA, 1.0 grams of GMA and 1.1 grams of TMPTMA. The mixture was degassed while applying vigorous stirring. The mixture was dispensed into molds and polymerized at 70° C. for eight hours, and post-cured at 95° C. for 10 hours. The molds were allowed to cool to room temperature. The molds were opened and the polymer disc was removed and inspected. The polymer displayed a glistening level of SI=826 on the Trattler Severity Index.

Comparative Example 3

18.5 grams of HPPA were mixed with 18.5 grams of EOEMA, 1.0 grams of HEA, 2.0 grams of GMA and 1.1 grams of TMPTMA. The mixture was degassed while applying vigorous stirring. The mixture was dispensed into molds and polymerized at 70° C. for eight hours, and post-cured at 95° C. for 10 hours. The molds were allowed to cool to room temperature. The molds were opened and the polymer disc was removed and inspected. The polymer displayed a glistening level of SI=850 on the Trattler Severity Index.

Comparative Example 4

26.0 grams of HPPA were mixed with 14 grams of EOEMA, and 1.1 grams of TMPTMA. The mixture was degassed while applying vigorous stirring. The mixture was dispensed into molds and polymerized at 70° C. for eight hours, and post-cured at 95° C. for 10 hours. The molds were allowed to cool to room temperature. The molds were opened and the polymer disc was removed and inspected. The polymer displayed a glistening level of SI=801 on the Trattler Severity Index.

Refractive Index Measurements

Refractive index may be measured by methods known in the art. The values recited herein were measured by the following method.

Measurements were acquired using a Atago Multiwavelength Abbe refractometer at testing temperatures of 20° C.±2 and 35° C.±2. To the prism of the refractometer was applied a drop of 1-bromonaphthalene and the flat polymer was placed thereon and allowed to equilibrate for ten minutes. RI values were recorded for three to five additional discs of the same formula to achieve a dry measurement average value.

Wet readings were then carried out by hydrating the discs at 20° C.±2 for a minimum of 24 hours. The disc is placed in the refractometer and allowed it to equilibrate at 20° C.±2 for ten minutes. Measurements are then repeated at 35° C.±2.

Water Content Measurements

A set of five discs from the same batch of polymeric material were weighed and placed in an oven at 110° C.±10 for at least 1.5 hours. The dry discs were then weighed. The discs were next hydrated in saline solution for 48 hours. Next, the discs were removed from solution, blotted dry and reweighed. The change in weight was indicative of the water content of the IOL.

Opening Time Measurements

An IOL universal blank or a finished lens was folded with tweezers and placed in a saline solution at 20° C. The sample was then released and the amount of time that the IOL took to return to its original shape was recorded. The procedure was repeated at 35° C.

Severity Index Measurement

An IOL universal blank was placed in saline solution at room temperature for 12 hours. The fully immersed IOL was then inspected under magnification of 20×, with an angle of 30 to 55 degrees (can be adjusted for maximum vacuole visibility). The number, size and density of the glistenings were calculated by visual inspection.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present embodiments encompasses not only the entire group listed as a whole, but each member of the group individually and all possible subgroups of the main group. Accordingly, for all purposes, the present embodiments encompass not only the main group, but also the main group absent one or more of the group members. The present embodiments also envisage the explicit exclusion of one or more of any of the group members in the claimed embodiments.

All references, patents and publications disclosed herein are specifically incorporated by reference in their entireties and for all purposes as if fully set forth in their entireties. Unless otherwise specified, "a" or "an" means "one or more".

While preferred embodiments have been illustrated and described, it should be understood that changes and modifications can be made therein in accordance with ordinary skill in the art without departing from the embodiments in its broader aspects as defined in the following claims.

What is claimed is:

1. An intraocular lens comprising at least one copolymer comprising:
   (a) a first monomeric subunit comprising a polymerized 2-hydroxy-3-phenoxypropyl acrylate,
   (b) a second monomeric subunit comprising a polymerized 2-ethoxyethyl methacrylate,
   (c) a third monomeric subunit comprising a polymerized-polyethylene glycol monomethyl ether methacrylate with a polyethylene glycol molecular weight of 200 to 400, and
   (d) a trimethacrylate crosslinker subunit,
   wherein the polymerized 2-hydroxy-3-phenoxypropyl acrylate is 50% to 70%, by weight of the copolymer, and the polymerized 2-ethoxyethyl methacrylate is 20% to 35%, by weight of the copolymer, and the polymerized polyethylene glycol monomethyl ether methacrylate with a polyethylene glycol molecular weight of 200 to 400 is 5% to 15%, by weight of the copolymer, and the trimethacrylate crosslinker is 0.5 to 3%, by weight of the copolymer, wherein the intraocular lens when hydrated has an SI value of less than 800.

2. The intraocular lens of claim 1, wherein the copolymer has a glass transition temperature below 35° C.

3. The intraocular lens of claim 1, wherein the copolymer has a glass transition temperature of about −5° C. to about 5° C.

4. The intraocular lens of claim 1, wherein the copolymer has an equilibrium water content of about 5 wt. % or less.

5. The intraocular lens of claim 1, wherein the copolymer has an equilibrium water content of about 4 wt. % or less.

6. The intraocular lens of claim 1, wherein the lens has a central thickness of up to 1 mm and unfolds in less than or about 1 minute when placed in a saline solution at a temperature of 36° C.

7. The intraocular lens of claim 1, wherein the lens has a central thickness of up to 1 mm and unfolds in 5 to 10 seconds.

8. The intraocular lens of claim 1, wherein the SI value is less than 750.

9. A composition comprising at least one copolymer comprising:
   (a) a first monomeric subunit comprising a polymerized 2-hydroxy-3-phenoxypropyl acrylate,
   (b) a second monomeric subunit comprising a polymerized 2-ethoxyethyl methacrylate,
   (c) a third monomeric subunit comprising a polymerized-polyethylene glycol monomethyl ether methacrylate with a polyethylene glycol molecular weight of 200 to 400, and
   (d) a fourth monomeric subunit comprising a polymerized trimethacrylate crosslinker,
   wherein the polymerized 2-hydroxy-3-phenoxypropyl acrylate is 50% to 70%, by weight of the copolymer, and the polymerized 2-ethoxyethyl methacrylate is 20% to 35%, by weight of the copolymer, the polymerized polyethylene glycol monomethyl ether methacrylate with a polyethylene glycol molecular weight of 200 to 400 is 5% to 15%, by weight of the copolymer and the trimethacrylate crosslinker is 0.5 to 3% by weight of the copolymer.

10. The composition of claim 9, wherein the copolymer has a glass transition temperature below 35° C.

11. The composition of claim 9, wherein the copolymer has a glass transition temperature of about −5° C. to about 5° C.

12. The composition of claim 9, wherein the copolymer has an equilibrium water content of about 5 wt. % or less.

13. The composition of claim 9, wherein a hydrated intraocular lens made from the composition has an SI value of less than 800.

14. A method for making a composition comprising at least one copolymer comprising monomeric subunits comprising:
   preparing a co-monomer mixture comprising:
      (a) a first monomer 2-hydroxy-3-phenoxypropyl acrylate,
      (b) a second monomer 2-ethoxyethyl methacrylate,
      (c) a third monomer comprising polyethylene glycol monomethyl ether methacrylate with a polyethylene glycol molecular weight of 200 to 400, and
      (d) a fourth monomer that is a trimethacrylate crosslinker,
   wherein the first monomer is 50% to 70%, by weight of the co-monomer mixture, and the second monomer is 20% to 35%, by weight of the co-monomer mixture, and the polyethylene glycol monomethyl ether methacrylate with a polyethylene glycol molecular weight of 200 to 400 is 5% to about 15%, by weight of the co-monomer mixture, and the fourth monomer is 0.5 to 3% by weight of the co-monomer mixture;
   polymerizing the co-monomer mixture.

15. An intraocular lens comprising at least one copolymer consisting essentially of:
   (a) a first monomeric subunit comprising a polymerized 2-hydroxy-3-phenoxypropyl acrylate,
   (b) a second monomeric subunit comprising a polymerized 2-ethoxyethyl methacrylate,
   (c) a third monomeric subunit comprising a polymerized-polyethylene glycol monomethyl ether methacrylate with a polyethylene glycol molecular weight of 200 to 400, and
   (d) one or more fourth monomeric subunits that is a trimethacrylate crosslinker,
   wherein the first monomeric subunit is present in a greater amount by weight than the second monomeric subunit, and the first and second monomeric subunits together consist essentially of 75 percent or more of the monomeric subunits by weight,
   wherein the polymerized 2-hydroxy-3-phenoxypropyl acrylate is 50% to 70%, by weight of the copolymer, and the polymerized 2-ethoxyethyl methacrylate is 20% to 35%, by weight of the copolymer, the polymerized polyethylene glycol monomethyl ether methacrylate with a polyethylene glycol molecular weight of 200 to 400 is 5% to 15%, by weight of the copolymer, and the polymerized trimethacrylate crosslinker is 0.5 to 3% by weight of the copolymer.

16. The intraocular lens of claim 1, wherein the polymerized 2-hydroxy-3-phenoxypropyl acrylate is 60 percent to 65 percent by weight of the copolymer; the polymerized 2-ethoxyethyl methacrylate is 27 percent to 32 percent by weight of the polymer; and the polymerized-polyethylene glycol monomethyl ether methacrylate with a polyethylene glycol molecular weight of 200 to 400 is 7 percent to 10 percent by weight of the copolymer.

17. The intraocular lens of claim 1, wherein the polymerized 2-ethoxyethyl methacrylate is 27 percent to 32 percent by weight of the copolymer.

18. The intraocular lens of claim 1, wherein the polymerized polyethylene glycol monomethyl ether methacrylate with a polyethylene glycol molecular weight of 200 to 400 is 7 percent to 10 percent by weight of the copolymer.

19. The intraocular lens of claim 1, wherein the polymerized polyethylene glycol monomethyl ether methacrylate with a polyethylene glycol has a molecular weight of 200.

20. The intraocular lens of claim 1, wherein the polymerized polyethylene glycol monomethyl ether methacrylate with a polyethylene glycol has a molecular weight of 400.

21. The intraocular lens of claim 16, wherein the polymerized polyethylene glycol monomethyl ether methacrylate with a polyethylene glycol has a molecular weight of 200.

22. The intraocular lens of claim 16, wherein the polymerized polyethylene glycol monomethyl ether methacrylate with a polyethylene glycol has a molecular weight of 400.

23. The intraocular lens of claim 17, wherein the polymerized polyethylene glycol monomethyl ether methacrylate with a polyethylene glycol has a molecular weight of 200.

24. The intraocular lens of claim 17, wherein the polymerized polyethylene glycol monomethyl ether methacrylate with a polyethylene glycol has a molecular weight of 400.

25. The intraocular lens of claim 18, wherein the polymerized polyethylene glycol monomethyl ether methacrylate with a polyethylene glycol has a molecular weight of 200.

26. The intraocular lens of claim 18, wherein the polymerized polyethylene glycol monomethyl ether methacrylate with a polyethylene glycol has a molecular weight of 400.

27. The method of claim 14, wherein the co-monomer mixture is polymerized in the absence of a solvent.

* * * * *